(12) United States Patent
Fukui

(10) Patent No.: US 8,691,997 B2
(45) Date of Patent: Apr. 8, 2014

(54) PROCESSES FOR PRODUCING 2-CHLORO-3-TRIFLUOROMETHYLPYRIDINE

(75) Inventor: Fumihiro Fukui, Shiga (JP)

(73) Assignee: Ishihara Sangyo Kaisha, Ltd, Osaka (JP)

( * ) Notice: Subject to any disclaimer, the term of this patent is extended or adjusted under 35 U.S.C. 154(b) by 0 days.

(21) Appl. No.: 13/518,584

(22) PCT Filed: Dec. 22, 2010

(86) PCT No.: PCT/JP2010/073252
§ 371 (c)(1),
(2), (4) Date: Jun. 22, 2012

(87) PCT Pub. No.: WO2011/078296
PCT Pub. Date: Jun. 30, 2011

(65) Prior Publication Data
US 2012/0259125 A1    Oct. 11, 2012

(30) Foreign Application Priority Data
Dec. 25, 2009    (JP) .................................. 2009-293768

(51) Int. Cl.
*C07D 211/72* (2006.01)

(52) U.S. Cl.
USPC ....................................................... 546/345

(58) Field of Classification Search
None
See application file for complete search history.

(56) References Cited

U.S. PATENT DOCUMENTS

| 4,393,214 A | 7/1983 | Roberts et al. |
| 4,897,488 A | 1/1990 | Gallenkamp et al. |

FOREIGN PATENT DOCUMENTS

| CN | 101454002 A | 6/2009 |
| EP | 0013474 A2 | 7/1979 |
| JP | 5581860 A | 6/1980 |
| JP | 55122762 A | 9/1980 |
| JP | 6220020 A | 8/1994 |
| JP | 2009531439 A | 9/2009 |
| WO | 2007126765 A2 | 11/2007 |
| WO | WO 2007126765 A2 * | 11/2007 |

OTHER PUBLICATIONS

Yamanaka Chem Pharm Bull 1988 pp. 2244-2247.*
CAPLUS 1981 15573.*
Yamanaka, H. et. al. "Site-Selective in the Reaction of 3-Substituted Pyrdine 1-Oxides with Phosphoryl Chloride", Chem. Pharm. Bull., vol. 36, No. 6, 1988, pp. 2244-2247 English.
International Search Report (PCT/ISA/210) issued on Mar. 15, 2011 in the International Patent Application No. PCT/JP2010/073252.
Written Opinion (PCT/ISA/237) issued on Mar. 15, 2011 in the International Patent Application No. PCT/JP2010/073252.
Communication dated May 23, 2013 from the State Intellectual Property Office of P.R. China in counterpart Chinese application No. 201080059179.8.

* cited by examiner

*Primary Examiner* — Heidi Reese
(74) *Attorney, Agent, or Firm* — Sughrue Mion, PLLC

(57) ABSTRACT

The present invention provides processes for producing 2-chloro-3-trifluoromethylpyridine which is useful as an intermediate for medicines and agrochemicals, at a high production rate in a high yield. Specifically, the present invention relates to a process for producing 2-chloro-3-trifluoromethylpyridine or a salt thereof comprising allowing 3-trifluoromethylpyridine N-oxide to react with a chlorinating agent; and also relates to a process for producing 2-chloro-3-trifluoromethylpyridine or a salt thereof comprising oxidizing 3-trifluoromethylpyridine to produce 3-trifluoromethylpyridine N-oxide and subsequently allowing the obtained 3-trifluoromethylpyridine N-oxide to react with a chlorinating agent.

4 Claims, No Drawings

PROCESSES FOR PRODUCING 2-CHLORO-3-TRIFLUOROMETHYLPYRIDINE

TECHNICAL FIELD

The present invention relates to processes for producing 2-chloro-3-trifluoromethylpyridine which is useful as an intermediate for medicines and agrochemicals.

BACKGROUND ART

Each of Patent Documents 1 and 2 describes a process for producing 2-chloro-3-trifluoromethylpyridine by allowing 3-trifluoromethylpyridine to react with chlorine, but they were not always satisfactory from the standpoint of production rate of 2-chloro-3-trifluoromethylpyridine.

Non-Patent Document 1 describes a process for producing ethyl 2-chloro-3-pyridinecarboxylate by allowing 3-ethoxycarbonylpyridine N-oxide to react with phosphorus oxychloride, but it does not describe a production process of 2-chloro-3-trifluoromethylpyridine.

CITATION LIST

Patent Documents

Patent Document 1: U.S. Pat. No. 4,393,214
Patent Document 2: JP-A-55-122762

Non-Patent Document

Non-Patent Document 1: *Chem. Pharm. Bull.*, 36(6), pages 2244 to 2247, 1988

SUMMARY OF THE INVENTION

Problem to be Solved by the Invention

A process for producing 2-chloro-3-trifluoromethylpyridine at a high production rate in a high yield is provided.

Means for Solving the Problem

As a result of various investigations for the purpose of solving the foregoing problem, a process for producing 2-chloro-3-trifluoromethylpyridine at a high production rate in a high yield by allowing 3-trifluoromethylpyridine N-oxide to react with a chlorinating agent has been found. In addition, a process for producing 2-chloro-3-trifluoromethylpyridine at a high production rate in a high yield by oxidizing 3-trifluoromethylpyridine to produce 3-trifluoromethylpyridine N-oxide and subsequently allowing the obtained 3-trifluoromethylpyridine N-oxide to react with a chlorinating agent.

Specifically, the present invention relates to a process for producing 2-chloro-3-trifluoromethylpyridine or a salt thereof comprising allowing 3-trifluoromethylpyridine N-oxide to react with a chlorinating agent; and also relates to a process for producing 2-chloro-3-trifluoromethylpyridine or a salt thereof comprising oxidizing 3-trifluoromethylpyridine to produce 3-trifluoromethylpyridine N-oxide and subsequently allowing the obtained 3-trifluoromethylpyridine N-oxide to react with a chlorinating agent.

Effect of the Invention

According to the production processes of the present invention, 2-chloro-3-trifluoromethylpyridine can be produced at a high production rate in a high yield.

EMBODIMENTS FOR CARRYING OUT THE INVENTION 2-chloro-3-trifluoromethylpyridine can be produced by allowing 3-trifluoromethylpyridine N-oxide to react with a chlorinating agent. In addition, a salt of 2-chloro-3-trifluoromethylpyridine can be produced in accordance with a usual salt forming reaction, and examples of the salt include acid addition salts such as hydrochlorides and sulfates, and the like.

[Chem. 1]

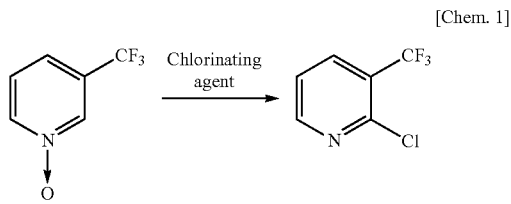 [SMILES: [O-][n+]1cccc(C(F)(F)F)c1 ; FC(F)(F)c1cccnc1Cl]

Examples of the chlorinating agent include acid chlorides such as acetyl chloride, trichloroacetyl chloride, and benzoyl chloride; sulfonic acid chlorides such as methanesulfonyl chloride and benzenesulfonyl chloride; quaternary ammonium salts such as tetraethylammonium chloride and tetrabutylammonium chloride; phosgene, diphosgene, triphosgene, oxalyl chloride, phosphorus trichloride, phosphorus oxychloride, phosphorus pentachloride, thionyl chloride, sulfuryl chloride, hydrogen chloride, and the like. Of these, oxalyl chloride, phosphorus oxychloride, and the like are preferable, with oxalyl chloride being more preferable. In particular, when oxalyl chloride is used as the chlorinating agent, the production rate and yield of 2-chloro-3-trifluoromethylpyridine are conspicuously enhanced.

In general, the chlorinating agent can be used in an amount of preferably from 1 to 10 times by mole, and more preferably from 1 to 3 times by mole per 1 mole of 3-trifluoromethylpyridine N-oxide. However, an amount falling outside this range can be adopted, depending upon reaction conditions.

In general, this reaction can be carried out in the presence of a solvent. The solvent is not particularly limited so far as it is inert to the reaction. Examples of the solvent include aliphatic hydrocarbons such as pentane, hexane, heptane, octane, and cyclohexane; aromatic hydrocarbons such as benzene, toluene, and xylene; halogenated hydrocarbons such as chlorobenzene, dichlorobenzene, dichloromethane, and dichloroethane; ethers such as diethyl ether, butyl ethyl ether, methyl tert-butyl ether, tetrahydrofuran, dioxane, and dimethoxyethane; polar aprotic solvents such as acetonitrile, propionitrile, N,N-dimethylformamide, dimethyl sulfoxide, sulfolane, N,N-dimethylacetamide, and N-methylpyrrolidone; esters such as methyl acetate, ethyl acetate, and propyl acetate; ketones such as acetone, methyl ethyl ketone, and methyl isobutyl ketone; and the like. Of these, halogenated hydrocarbons are preferable, and dichloromethane and dichloroethane are more preferable. In particular, when dichloromethane or dichloroethane is used as the solvent, the production rate and yield of 2-chloro-3-trifluoromethylpyridine are conspicuously enhanced.

This reaction can be carried out in the presence of a base, if necessary. Examples of the base include alkali metal carbonates such as sodium carbonate and potassium carbonate; alkali metal bicarbonates such as sodium bicarbonate and potassium bicarbonate; alkali metal acetates such as sodium acetate and potassium acetate; tertiary amines such as trimethylamine, triethylamine, diisopropylamine, triisopropylamine, diisopropylethylamine, pyridine, 4-dimethylaminopyridine, 2,6-dimethylpyridine, 4-pyrrolidinopyridine, N-methylmorpholine, N,N-dimethylaniline, N,N-diethylaniline, N-ethyl-N-methylaniline, 1,8-diazabicyclo[5.4.0]-7-undecene, and 1,4-diazabicyclo[2.2.2]octane; and the like. Of these, tertiary amines are preferable, and triethylamine is more preferable. In particular, when triethylamine is used as the base, the production rate and yield of 2-chloro-3-trifluoromethylpyridine are conspicuously enhanced.

In general, the base can be used in an amount of preferably from 1 to 10 times by mole, and more preferably from 1 to 3 times by mole per 1 mole of 3-trifluoromethylpyridine N-oxide. However, an amount falling outside this range can be adopted, depending upon reaction conditions.

In addition, in the case of using the base, the base and the chlorinating agent can be added in an arbitrary order. For example, the base may be added before or after adding the chlorinating agent, or may be added simultaneously with the chlorinating agent. In particular, in the case of using the base, when the base is added after adding the chlorinating agent, the production rate and yield of 2-chloro-3-trifluoromethylpyridine are conspicuously enhanced.

In general, a reaction temperature is preferably from about −60 to 150° C., and more preferably from about −40 to 130° C. In general, a reaction time is preferably from about 0.1 to 24 hours, and more preferably from about 0.5 to 12 hours. In the case of using oxalyl chloride as the chlorinating agent, in general, the reaction temperature is preferably from about −40 to 20° C., and more preferably from about −30 to 10° C. In the case of using oxalyl chloride as the chlorinating agent, when the reaction temperature is preferably from −40 to 20° C., and more preferably from −30 to 10° C., the production rate and yield of 2-chloro-3-trifluoromethylpyridine are conspicuously enhanced.

2-Chloro-3-trifluoromethylpyridine can be produced by oxidizing 3-trifluoromethylpyridine to produce 3-trifluoromethylpyridine N-oxide and subsequently allowing the obtained 3-trifluoromethylpyridine N-oxide to react with a chlorinating agent. On that occasion, 3-trifluoromethylpyridine N-oxide can be allowed to react with the chlorinating agent without being isolated or purified.

[Chem. 2]

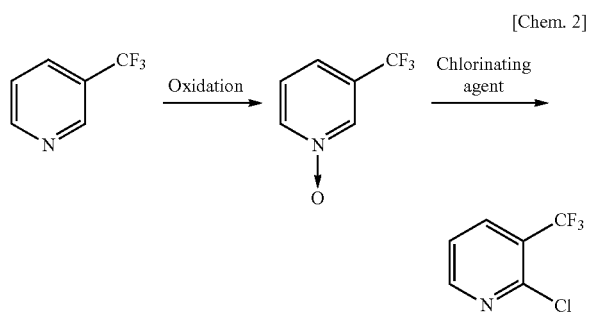

The reaction between 3-trifluoromethylpyridine N-oxide and the chlorinating agent is the same as described above.

The oxidation is carried out by allowing 3-trifluoromethylpyridine to react with an oxidizing agent. Examples of the oxidizing agent include peracids such as peracetic acid, perbenzoic acid, and m-chloroperbenzoic acid; hydroperoxides such as cumyl hydroperoxide and tert-amyl hydroperoxide; hydrogen peroxide; and the like. Of these, peracetic acid, tert-amyl hydroperoxide, hydrogen peroxide, and the like are preferable.

In general, the oxidizing agent can be used in an amount of preferably from 1 to 10 times by mole, and more preferably from 1 to 3 times by mole per 1 mole of 3-trifluoromethylpyridine. However, an amount falling outside this range can be adopted, depending upon reaction conditions.

In general, this reaction can be carried out in the presence of a solvent. The solvent is not particularly limited so far as it is inert to the reaction. Examples of the solvent include aliphatic hydrocarbons such as pentane, hexane, heptane, octane, and cyclohexane; aromatic hydrocarbons such as benzene, toluene, and xylene; halogenated hydrocarbons such as chlorobenzene, dichlorobenzene, dichloromethane, and dichloroethane; organic acids such as acetic acid and propionic acid; water; and the like.

In general, a reaction temperature is preferably from about 0 to 150° C., and more preferably from about 10 to 120° C. In general, a reaction time is preferably from about 0.1 to 24 hours, and more preferably from about 0.5 to 12 hours.

EXAMPLES

In order to describe the present invention in more detail, Examples are described below, but it should not be construed that the present invention is limited thereto.

Example 1

(1) In a four-necked flask equipped with a stirrer, a thermometer, and a condenser, 147.0 g of 3-trifluoromethylpyridine and 367.75 g of acetic acid were charged. 141.71 g of a 30% hydrogen peroxide aqueous solution was added thereto at from 20 to 30° C., and the contents were allowed to react at from 80 to 90° C. for 7 hours.

After the reaction mixture was cooled, 31.51 g of sodium sulfite was added at not higher than 30° C. After the addition, the contents were stirred at from 30 to 40° C. for 3 hours, and it was confirmed by a potassium iodide starch paper that the treatment of excessive hydrogen peroxide in the reaction mixture had been completed.

The reaction mixture was heated under a reduced pressure (15 mmHg) until the internal temperature reached 50° C., thereby distilling off the acetic acid. 441 mL of water was added thereto, and 204.26 g of a 30% sodium hydroxide aqueous solution was added dropwise at not higher than 20° C., thereby adjusting the pH to 8.0. Thereafter, extraction with 275.6 g of 1,2-dichloroethane was repeated three times while keeping the temperature at 50° C., thereby obtaining 985.0 g of a 1,2-dichloroethane solution containing 158.16 g of 3-trifluoromethylpyridine N-oxide (melting point: 76.0° C.).

(2) In a four-necked flask equipped with a stirrer, a thermometer, a drying tube, and a dropping funnel, 35.47 g of a 1,2-dichloroethane solution containing 4.89 g of 3-trifluoromethylpyridine N-oxide (13.78% solution) was charged. 4.57 g of oxalyl chloride was added dropwise thereto at from −30 to −20° C., and the contents were allowed to react at the same temperature for one hour. To the reaction mixture, a mixed solution of 3.64 g of triethylamine and 6.1 g of 1,2-dichloroethane was added dropwise at from −30 to −20° C.

over one hour, and the contents were further allowed to react at the same temperature for 2 hours. The reaction mixture was analyzed by means of liquid chromatography and confirmed to contain 0.35% of 3-trifluoromethylpyridine N-oxide, 91.89% of 2-chloro-3-trifluoromethylpyridine, and 0.72% of 2-chloro-5-trifluoromethylpyridine.

The reaction mixture was added to 24.45 g of ice water at not higher than 10° C. and stirred at from 10 to 20° C. for 30 minutes, followed by liquid separation. The obtained organic layer was washed with water to obtain 43.1 g of a 1,2-dichloroethane solution containing 2-chloro-3-trifluoromethylpyridine. The obtained solution was analyzed by means of liquid chromatography and confirmed to contain 4.25 g of 2-chloro-3-trifluoromethylpyridine in the solution.

Example 2

In a four-necked flask equipped with a stirrer, a thermometer, and a drying tube, 32.62 g of 3-trifluoromethylpyridine N-oxide and 46.0 g of phosphorus oxychloride were charged, and the contents were allowed to react at from 105 to 110° C. for 2 hours. Subsequently, the contents were further allowed to react at from 120 to 125° C. for 5 hours. The reaction mixture was analyzed by means of liquid chromatography and confirmed to contain 0.16% of 3-trifluoromethylpyridine N-oxide, 50.34% of 2-chloro-3-trifluoromethylpyridine, and 25.34% of 2-chloro-5-trifluoromethylpyridine.

The reaction mixture was heated under a reduced pressure (100 mmHg) until the internal temperature reached 75° C., thereby distilling off excessive phosphorus oxychloride. The reaction mixture was added to 163.1 g of ice water and stirred at not higher than 30° C. for one hour. Thereafter, the resultant was extracted with 1,2-dichloroethane and stirred for 30 minutes to conduct liquid separation. The obtained organic layer was washed with water to obtain 132.11 g of a 1,2-dichloroethane solution containing 2-chloro-3-trifluoromethylpyridine. The obtained solution was analyzed by means of liquid chromatography and confirmed to contain 13.17 g of 2-chloro-3-trifluoromethylpyridine in the solution.

Example 3

(1) In a four-necked flask equipped with a stirrer, a thermometer, and a condenser, 238.63 g of 3-trifluoromethylpyridine and 596.57 g of acetic acid were charged. 229.85 g of a 30% hydrogen peroxide aqueous solution was added thereto at from 20 to 30° C., and the contents were allowed to react at from 80 to 90° C. for 7 hours.

After the reaction mixture was cooled, 51.11 g of sodium sulfite was added at not higher than 30° C. After the addition, the contents were stirred at from 30 to 40° C. for 3 hours, and it was confirmed by a potassium iodide starch paper that the treatment of excessive hydrogen peroxide in the reaction mixture had been completed.

The reaction mixture was heated under a reduced pressure (15 mmHg) until the internal temperature reached 55° C., thereby distilling off the acetic acid. 357.9 mL of water was added thereto, and 343.2 g of a 30% sodium hydroxide aqueous solution was added dropwise at not higher than 15° C., thereby adjusting the pH to 8.0. Thereafter, extraction with 633.1 g of dichloromethane was repeated twice while keeping the temperature at from 30 to 40° C. Subsequently, the dichloromethane extracted solution was heated at atmospheric pressure until the internal temperature reached 50° C., thereby not only distilling off the dichloromethane but removing water within the system. There was thus obtained 811.9 g of a dichloromethane solution containing 259.57 g of 3-trifluoromethylpyridine N-oxide (melting point: 76.0° C.).

(2) In a four-necked flask equipped with a stirrer, a thermometer, a drying tube, and a dropping funnel, 637.70 g of a dichloromethane solution containing 203.88 g of 3-trifluoromethylpyridine N-oxide (31.97% solution) and 918.5 g of dichloromethane were charged. 190.4 g of oxalyl chloride was added dropwise thereto at from −30 to −20° C., and the contents were allowed to react at the same temperature for one hour. To the reaction mixture, a mixed solution of 151.97 g of triethylamine and 135.0 g dichloromethane was added dropwise at from −30 to −20° C. over one hour, and the contents were further allowed to react at the same temperature for 2 hours. The reaction mixture was analyzed by means of liquid chromatography and confirmed to contain 0.24% of 3-trifluoromethylpyridine N-oxide, 90.93% of 2-chloro-3-trifluoromethylpyridine, and 0.52% of 2-chloro-5-trifluoromethylpyridine.

The reaction mixture was added to 1,019.3 g of ice water at not higher than 10° C. and stirred at from 10 to 20° C. for one hour, followed by liquid separation. To the obtained organic layer, 407.8 g of water was added, and 26.7 g of a 30% sodium hydroxide aqueous solution was added dropwise at from 20 to 30° C., thereby adjusting the pH to 8.0, followed by stirring at the same temperature for 2 hours. Thereafter, liquid separation was conducted to obtain 1,531 g of a dichloromethane solution containing 2-chloro-3-trifluoromethylpyridine. The dichloromethane was distilled off from the obtained solution at atmospheric pressure, and the residue was heated until the internal temperature reached 90° C. Thereafter, fractions until the internal temperature reached 100° C. under a reduced pressure (38 mmHg) were collected to obtain 161.27 g of 2-chloro-3-trifluoromethylpyridine having a purity of 99.27%.

Example 4

In a four-necked flask equipped with a stirrer, a thermometer, a drying tube, and a dropping funnel, 23.65 g of a 1,2-dichloroethane solution containing 3.26 g of 3-trifluoromethylpyridine N-oxide (13.78% solution) was charged. 3.05 g of oxalyl chloride was added dropwise thereto at from 0 to 5° C., and the contents were allowed to react at the same temperature for one hour. To the reaction mixture, a mixed solution of 2.42 g of triethylamine and 4.08 g of 1,2-dichloroethane was added dropwise over one hour at from 0 to 10° C., and the contents were further allowed to react at the same temperature for 2 hours. The reaction mixture was analyzed by means of liquid chromatography and confirmed to contain 39.72% of 3-trifluoromethylpyridine N-oxide, 54.63% of 2-chloro-3-trifluoromethylpyridine, and 1.31% of 2-chloro-5-trifluoromethylpyridine.

Example 5

In a four-necked flask equipped with a stirrer, a thermometer, a drying tube, and a dropping funnel, 124.49 g of the dichloromethane solution containing 16.31 g of 3-trifluoromethylpyridine N-oxide (13.10% solution) was charged. 12.69 g of oxalyl chloride was added dropwise thereto at from −30 to −20° C., and the contents were allowed to react at the same temperature for one hour. To the reaction mixture, a mixed solution of 10.12 g of triethylamine and 10.82 g of dichloromethane was added dropwise over one hour at from −30 to −20° C., and the contents were further allowed to react at the same temperature for 2 hours. The reaction mixture was analyzed by means of liquid chromatography and confirmed to contain 5.47% of 3-trifluoromethylpyridine N-oxide, 85.57% of 2-chloro-3-trifluoromethylpyridine, and 0.42% of 2-chloro-5-trifluoromethylpyridine.

The reaction mixture was added to 81.55 g of ice water at not higher than 10° C. and stirred at from 10 to 20° C. for one hour, followed by liquid separation. The obtained organic layer was washed with water to obtain 143.25 g of a dichloromethane solution containing 2-chloro-3-trifluoromethylpyridine. The obtained solution was analyzed by means of liquid chromatography and confirmed to contain 14.18 g of 2-chloro-3-trifluoromethylpyridine.

While the present invention has been described in detail with reference to specific embodiments thereof, it will be apparent to one skilled in the art that various changes and modifications can be made therein without departing from the spirit and scope thereof.

Incidentally, the present application is based on a Japanese patent application filed on Dec. 25, 2009 (Japanese Patent Application No. 2009-293768), the entire contents of which are incorporated hereinto by reference.

In addition, All reference cited herein are incorporated in their entirety.

[Industrial Applicability]

According to the production processes of the present invention, 2-chloro-3-trifluoromethylpyridine can be produced at a high production rate in a high yield.

The invention claimed is:

1. A process for producing 2-chloro-3-trifluoromethylpyridine or a salt thereof comprising allowing 3-trifluoromethylpyridine N-oxide to react with a chlorinating agent, wherein the chlorinating agent is oxalyl chloride.

2. The process according to claim 1 wherein the 3-trifluoromethylpyridine N-oxide is produced by oxidizing 3-trifluoromethylpyridine.

3. The process according to claim 1 or 2, wherein the chlorinating agent is used in an amount of from 1 to 10 times by mole per 1 mole of 3-trifluoromethylpyridine N-oxide.

4. The process according to claim 1 or 2, wherein the reaction between 3-trifluoromethylpyridine N-oxide and the chlorinating agent is conducted at a reaction temperature of from −40 to 20° C.

* * * * *